(12) United States Patent
Pietronigro et al.

(10) Patent No.: US 6,753,005 B1
(45) Date of Patent: Jun. 22, 2004

(54) METHOD FOR TISSUE PERFUSION (75) Inventors: Dennis Pietronigro, Katonah, NY (US); Vincent Decrescito, Malverne Park, NY (US); Richard Kronenthal, Fairlawn, NJ (US); Dean McBeth, Croton-On-Hudson, NY (US)

(73) Assignee: Direct Therapeutics, Inc., Redwood City, CA (US)

( * ) Notice: Subject to any disclaimer, the term of this patent is extended or adjusted under 35 U.S.C. 154(b) by 0 days.

(21) Appl. No.: 09/458,541

(22) Filed: Dec. 10, 1999

Related U.S. Application Data (62) Division of application No. 09/224,599, filed on Dec. 31, 1998.
(60) Provisional application No. 60/070,175, filed on Dec. 31, 1997.

(51) Int. Cl.[7] .......................... A61F 13/00; A61K 9/66; A61N 47/34
(52) U.S. Cl. ................... 424/422; 424/455; 514/589; 514/937
(58) Field of Search ................. 424/1.11, 1.25, 424/423, 422, 424, 425, 426, 427, 428, 405, 455; 514/937, 589

(56) References Cited

U.S. PATENT DOCUMENTS

| | | | |
|---|---|---|---|
| 3,957,996 A | | 5/1976 | Adams et al. |
| 3,966,934 A | | 6/1976 | Adams et al. |
| 4,536,387 A | * | 8/1985 | Sakamoto et al. ............. 424/14 |
| 5,023,271 A | * | 6/1991 | Vigne et al. ................. 514/458 |
| 5,051,257 A | | 9/1991 | Pietronigro |
| 5,162,115 A | * | 11/1992 | Pietronigro et al. ........ 424/423 |
| 5,610,173 A | * | 3/1997 | Schwartz et al. ........... 514/378 |
| 5,789,244 A | | 8/1998 | Heidrun et al. |
| 5,851,527 A | | 12/1998 | Hansen |

OTHER PUBLICATIONS

American Society of Hospital Pharmacists (ASHP), Drug Information Manual, Listing for Carmustine, section 10:00, 1994 edition.*

* cited by examiner

Primary Examiner—Michael G. Hartley
(74) Attorney, Agent, or Firm—Darby & Darby

(57) ABSTRACT

Disclosed are compositions and methods for the facile perfusion of a tissue with active agents following direct intra-tissue injection. Targets may consist of cells, cellular components, and/or extracellular components. The high perfusion efficiency permits high concentrations of active agents to be delivered to tissue targets resulting in high degrees of efficacy and in some instances the production of novel pharmacological activities of an active agent previously unknown or previously unattainable in vivo.

25 Claims, 3 Drawing Sheets

METHOD FOR TISSUE PERFUSION

The present application is a divisional application of U.S. application Ser. No. 09/224,599, filed Dec. 31, 1998, which claims the benefit of priority of U.S. Provisional Application No. 60/070,175, filed Dec. 31, 1997. The disclosure of each of the foregoing applications is hereby incorporated herein by reference, in its entirety.

FIELD OF THE INVENTION

This invention relates to compositions and methods for producing facile perfusion of active agents in tissues following direct intra-tissue delivery. In another aspect it relates to compositions and methods to identify those compositions capable of producing novel pharmacological activities of an active agent following intra-tissue delivery.

BACKGROUND

The inability of agents to perfuse throughout a tissue, permeate cells and achieve biologically effective levels at their targets has been a longstanding problem in the field of drug delivery. Methods to overcome this include targeting of active agents to tissues by:

Use of delivery vehicles which are targeted to specific receptors on the surface of cells (e.g. monoclonal antibodies,)—this is limited by the inadequate diffusion of the antibody-active agent conjugates through solid tissue.

Use of active agents whose targets are only expressed in target cells (e.g. DNA with tissue specific promoters)—these are limited by the inability of vectors delivering these agents to access large numbers of cells through solid tissue, production of efficacious amounts of active agents and potential dangers which viral vectors/DNA presents in the target and surrounding cells.

Conjugating the active agent to low density lipoprotein (LDL) for internalization via the cell membrane LDL receptor has been attempted to overcome physiological barriers which obstruct systemic drug delivery to target tissue (e.g. capture of agents by proteins in solution in the blood and the inability of many agents to effectively cross the blood-brain barrier). Again, this results in a lack of specificity of agent delivery and problems in obtaining adequate amounts of agents at their target sites. High flow microinfusion has been attempted to achieve an increase in drug delivery across the blood-brain barrier.

Use of liposomes to encapsulate agents in the hydrophilic aqueous interspaces or in the lipid bilayer for hydrophobic compounds is another delivery method limited by the inability to achieve adequate targeting and perfusion through solid tissue.

Antineoplastic solutions consisting of an organic water miscible solvent vehicle containing an antineoplastic agent solute have been previously shown to be effective for the rapid and effective perfusion of solid tumors (Pietronigro 1991 U.S. Pat. No. 5,051,257 and Pietronigro 1992, U.S. Pat. No. 5,162,115).

The effective perfusion through non-neoplastic tissues, however, remains a problem. Non-neoplastic mammalian tissues are tissues or tissue regions not comprised entirely of a new and abnormal formation of tissue such as a solid palpable tumor, but rather, a tissue comprised essentially of original normal tissue which now, in part, contains: abnormal (i.e., damaged or diseased) tissue components, e.g., dispersed, individual cancerous cells, ischemic cells, thrombosed blood vessels, cells expressing specific aberrant gene products(s), cells producing specific gene products in abnormal quantities or unnatural extracellular accumulations of substances; and/or foreign elements, e.g., infectious agents such as bacteria and viruses and fungi. Mixed tissues are tissues containing both regions of normal tissue and regions of non-neoplastic tissues.

While the structure of solid tumors is ideal for penetration by an organic water miscible solvent vehicle, delivering the agent to cells throughout the tumor, the structure of normal, non-neoplastic and mixed tissues presents many obstacles to effective penetration by active agents.

Tumors possess large quantities of interstitial space which can be up to six times greater than that found in normal tissue (Jain 1987, Cancer Research, 47, 3039–3051). A contributing factor to the increased interstitial space in tumors is the lower density of cells present. Cellular architecture and organization also varies greatly between tumors and normal tissue. The structural integrity found in normal tissues is a result of the presence of cell-cell junctions (e.g., tight junctions, desmosomes), cell-cell surface adhesion molecules (e.g., cadherins) and cell-basement membrane adhesion molecules (e.g. integrins). The cell-cell and cell-basement membrane attachments are reduced in tumors as a result of a decrease in the expression of molecules responsible for these interactions (Dvorak 1998, Critical issues in Tumor Microcirculation, Angiogenesis and Metastasis, Lecture 1, 1–17, St. Croix 1997, Current Opinion in Oncology, 9, 549–556). The cells in tumors grow in small clumps distributed throughout the interstitial space, with little cell-cell attachment, or structural integrity. Normal tissue consists of highly organized three-dimensional arrangements of cells, often many cell layers thick.

Tumor blood vessels lack the structural integrity of blood vessels in normal tissue. Tumor vessels are hyperpermeable (Dvorak 1998, Critical Issues in Tumor Microcirculation, Angiogenesis and Metastasis, Lecture 1, 1–17), and lack the normal basement membrane surrounding the vessels in normal tissue. The lymphatic system present in normal tissue is lacking in tumors. Fluid in the interstitial space is drained by lymphatic vessels in normal tissue. In tumors, there is a build up of fluid in the interstitium due to the absence of lymphatics and the hyperpermeability of the blood vessels which results in an increase in the pressure in the interstitial space. A pressure gradient exists in tumors, the highest pressure being at the tumor center and which decreases towards the edge of the tumor (Jain, 1997, Microcirculation, 4(1), 1–23).

The low cell density and increased interstitial space of solid tumors provides an ideal medium for the organic water miscible solvent vehicle to penetrate through. Arrangement of cells in clumps with little adhesion between them enables all cells throughout the tumor to be perfused with the antineoplastic solution. The interstitial pressure gradient that exists from the center to the outer edge of the tumor would aid perfusion of an antineoplastic solution injected into the tumor center.

In contrast non-neoplastic tissues having relatively small interstitial space coupled with the rigid cellular organization and structural integrity present many barriers to the transport of an active agent administered by direct injection. The high degree of cell-cell and cell-basement membrane interactions, high cell density and many cell layers present physical barriers to the distribution of an active agent. The lack of a pressure gradient is also believed to act to lessen distribution of a solution throughout the tissue. Thus, the effective perfusion through non-neoplastic tissues, normal tissue or mixed tissues remains a problem.

In view of the above, the limitations to the perfusion of tissues known to the prior art are readily apparent.

OBJECTS OF THE INVENTION

Accordingly it is an object of the present invention to provide compositions and a method for the facile perfusion of an active agent throughout a tissue.

Another object of the present invention is to provide compositions and a method to selectively affect a subset of tissue components by the facile perfusion of an active agent throughout a tissue.

Another object of the present invention is to provide compositions and a method to treat a tissue with a high (previously unobtainable) dose of an active agent.

Another object of the present invention is to provide compositions and a method for producing novel pharmacological activities of active agents in tissues.

Another object of the present invention is to provide compositions and a method to alter the spectrum of activity of an active agent attainable in vivo.

Another object of the present invention is to provide a method for the identification of novel pharmacological activities of an active agent.

Other objects and advantages of the present invention will, in part, be apparent and will, in part, appear hereinafter.

The manner in which these and other objects are realized by the present invention will be apparent from the summary and detailed description set forth below.

SUMMARY OF THE INVENTION

In accordance with the present invention facile perfusion of a mammalian tissue with an active agent is achieved by direct intra-tissue injection of solutions consisting of active agent solutes in water miscible organic solvent vehicles. The active agents are chosen to have solubility, stability and bioavailability in the water miscible organic solvent vehicle. Intra-tissue injection of these solutions permits high levels of active agent solute to readily permeate through the tissue and into cells thereby achieving heretofore unobtainable levels at target sites. The facile perfusion results in high degrees of efficacy and can produce selective effects on the abnormal tissue components and foreign elements of the tissue perfused and can also produce novel pharmacological or biochemical actions previously unknown or unattainable in vivo due to the high levels of active agent delivered to the tissue.

DETAILED DESCRIPTION OF THE INVENTION.

All patent applications, patents and literature references cited herein are hereby incorporated by reference in their entirety.

The present invention provides methods for the rapid and efficient penetration (i.e., facile perfusion) of tissue with an active agent by the direct injection into the tissue of a pharmaceutically acceptable organic water miscible solvent vehicle having a partition coefficient of at least about 0.1, and an active agent solute.

The solvent vehicles useful for facile perfusion of active agents are water miscible organic solvents which are soluble in water and which also partition and diffuse into and through biological cell membranes from aqueous solutions. Their usefulness is based not only upon their solvent power for the therapeutic agent, but also upon their ability to permeate the tissue effectively. In the solvent vehicles of the invention molecular movement through the aqueous phase is driven by the high water solubility of such vehicles which, in a preferred embodiment, is infinite or nearly so at physiologic conditions. Since the majority of tissue substance is aqueous, water miscibility or solubility of the organic solvent component is important. Additionally, the water miscible organic vehicles of the present invention have sufficient lipophilicity to move into cellular membranes from aqueous solution. Molecular characteristics that endow this ability are molecular weight of less than about one thousand Daltons, measured as described in Morrison and Boyd, Organic Chemistry, pp. 412–413, Allyn and Bacon Inc., Boston,1966, and electrical neutrality (that is, absence of charge) as demonstrated by molecular formula. A direct measure of molecular movement from aqueous solution into lipids is the partition coefficient as described, for example, by Cornford et al., "Comparison of Lipid-Mediated Blood-Brain-Barrier Penetrability in Neonates and Adults", in American Journal of Physiology 243 (1982), pp. C161–C168. The preferred water miscible organic solvents of the present invention have partition coefficients of at least about 0.1. Cornford et al.,supra, also demonstrate the close correlation between partition coefficients and true cellular membrane diffusivity measurement using the brain uptake index. Exemplary water miscible organic solvents possessing the foregoing characteristics and which are therefore useful as direct delivery vehicles in the present invention are: methanol, ethanol, 1-propanol, 2-propanol, 1-propen-3-ol(allyl alcohol), 2-methyl-2-propanol tertiary butyl alcohol), diacetonealcohol, N'N'-dimethylformamide, dimethylsulfoxide, 1,3-dioxane, acetone, pyridine, tetrahydrofuran, ethylene glycol and propylene glycol, used alone or in combination. The preferred solvent is absolute ethanol. In addition to these, other useful organic solvent vehicles can also be identified by their water solubility and biological membrane diffusivity. In contrast to the alcohols specifically listed above, the usefulness of 1-butanol would be somewhat limited while the use of aliphatic alcohols higher than C4 would be contra indicated for use in the invention due to the limited water solubilities such alcohols.

Active agents include those which are soluble in the above solvents (including antineoplastic agents such as BCNU or carmustine, hormones, cell membrane receptor ligands and antimetabolites) and which effect target cells, cellular components such as epithelial, endothelial and mesenchymal cells, or extracellular components such as extracellular matrix proteins, carbohydrates and lipids. One particularly useful active agent which is soluble in ethanol is carmustine (an anti-tumor agent).

The inability of an active agent to effectively permeate the aqueous environment of a tissue by diffusion or convection and attain therapeutic levels at its target without producing unwanted adverse side effects on non-target tissue is a major obstacle in the area of drug delivery. Furthermore, the inability of agents that are soluble in aqueous solutions to permeate the lipid cell membrane adds to this obstacle. To overcome these problems, delivery vehicles which are both miscible with the aqueous environment of the tissue and sufficiently lipophilic to permeate the cell membrane have been selected for use in the present invention. These vehicles can be utilized to deliver solutes which are stable and bioavailable in these solvents. The delivery vehicle and solute are injected directly into the tissue that is the target of the solute.

Figure 1A:
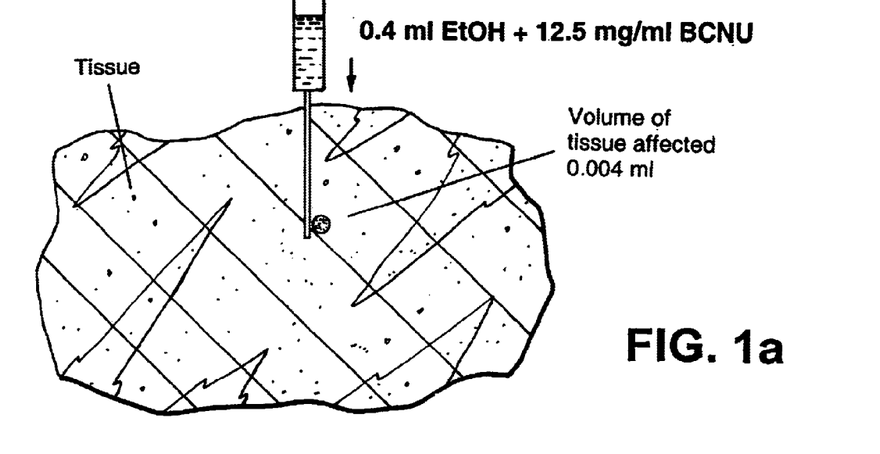
FIGS. 1a and 1b illustrate the effects of increasing concentration of BCNU on volume of tissue affected.
Figure 1B:
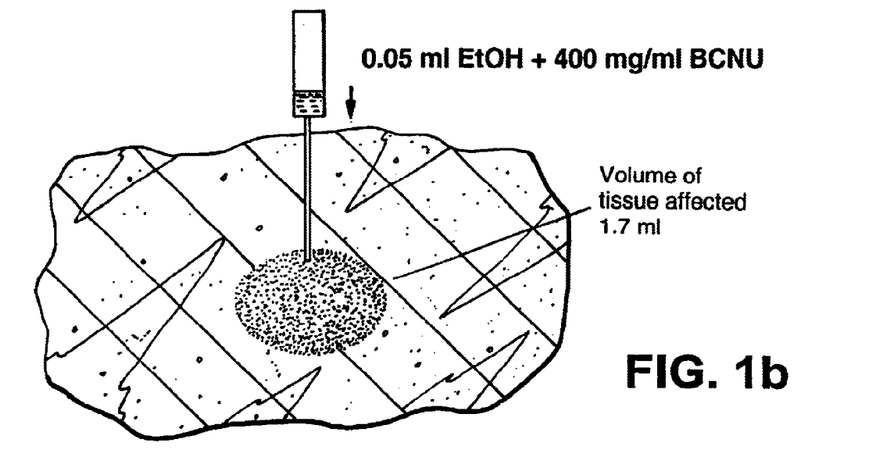
Figure 2:
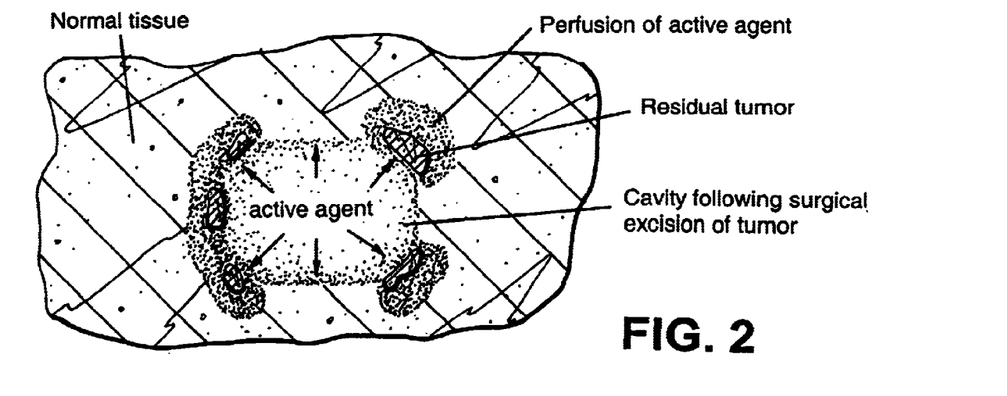
FIG. 2 illustrates perfusion of mixed tissue with an active agent following surgical resection of a tumor.
Figure 3A:
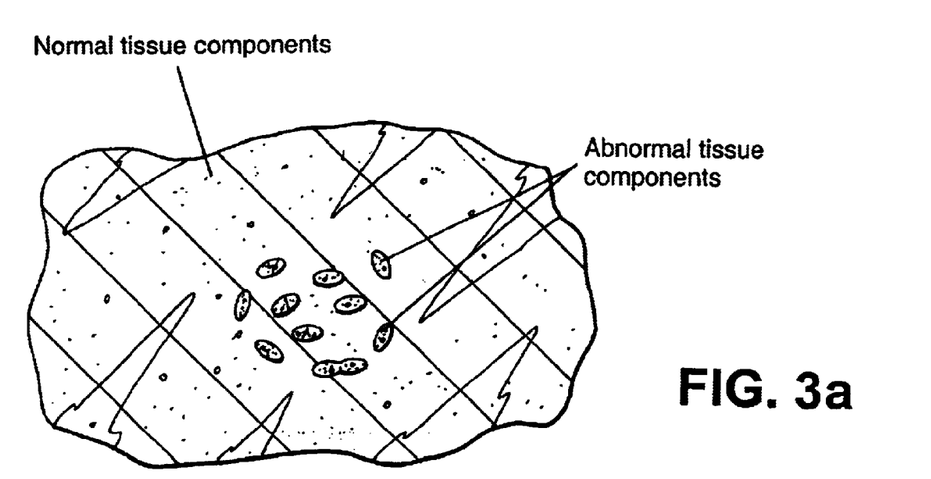
FIGS. 3a and 3b illustrate selective effects of an active agent on abnormal tissue components.
Figure 3B:
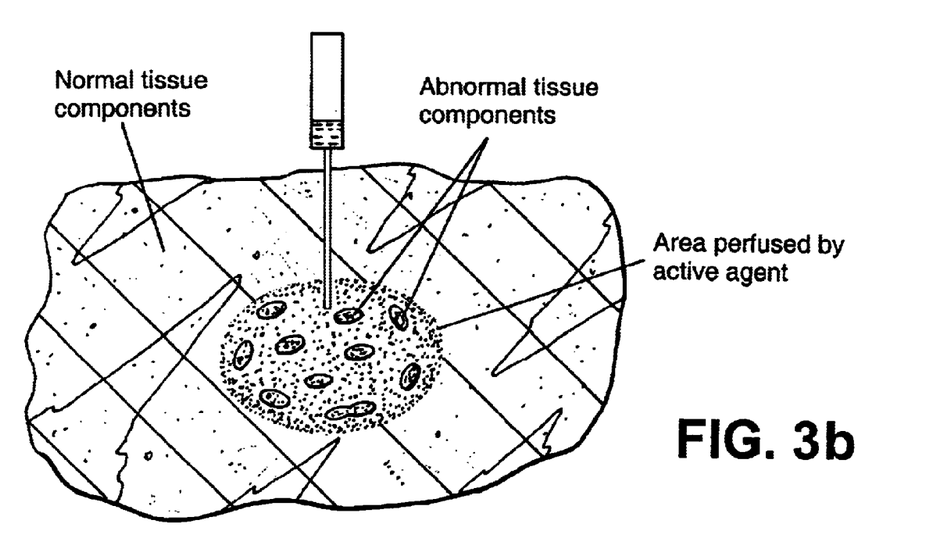

The active agent is preferably dissolved in the organic solvent to a concentration such that when a therapeutically effective volume of the solution of the invention is delivered into a tissue, there results a dose of the agent solute in said tissue of at least two logs greater than its effective dose 50% (ED50), that is, the dose of agent in said tissue that produces the desired therapeutic effect on 50% of the target cells. This ensures that a sufficient concentration of the agent is delivered throughout at least a substantial volume of the tissue when the resulting solution is injected directly into the tissue. As the organic vehicle permeates the tissue it transports a therapeutically effective concentration of the agent solute therewith. In this way high levels of the active agent can be delivered discretely and with relative safety to the tissue. The water miscible organic vehicle component of the solution can also be considered to be increasing the solubility of the agent within the tissue, thereby allowing therapeutically effective levels of the active agent to invest the tissue. It must also be appreciated that active agents with high solubility in the water miscible organic solvent vehicles of the invention will themselves usually tend to have good cellular diffusivity characteristics and can thus, upon direct in-the-tissue administration, diffuse relatively efficiently on their own, in many instances, beyond the perfusion zone of the solvent vehicle component. The stability and bioavailability of the active agent in the selected solvent vehicle aid in insuring that high levels of active agent permeate the tissue.

The invention includes the use of an imaging device for monitoring the perfusion of a tissue with an active agent and a method for the use of an imaging device for geographical assessment of the effects of an active agent upon a tissue.

The compositions and method of the invention can be employed to cause the facile perfusion of non-neoplastic tissue, normal tissue and mixed tissues with an active agent. The facile perfusion causes volumes of tissue much larger than the volume of solution injected to be effectively treated with an active agent. The compositions can be formulated so that the active agent produces selective effects upon one or more tissue components or foreign elements; produces novel pharmacological, biochemical or biological effects due to the high levels of active agent actually delivered to tissue target sites; and/or produces non-selective effects upon all the tissues regions and elements perfused.

Examples of non-neoplastic and mixed tissues which can be treated with the present invention include those infected with pathological agents, e.g., bacteria, viruses, fungi; brain tissue of Alzheimers patients; traumatized tissue, e.g., following head or spinal cord injury; arthritic tissue; tissue foci producing epileptic seizures; glaucomatous tissue; tissue undergoing inflammation; Parkinsons disease tissue; tissue containing diffuse cancer cells and micrometastases; tissue undergoing rheumatic disease; prostatic tissue undergoing benign hypertrophy; endometriosis tissue; osteoporosis tissue; mis-functioning central nervous system tissue producing depression, psychosis, or other nervous system disorders; ischemic tissue of the brain, heart and other organs; and tissues producing a pain response.

Modifications of the solutions developed can be used to adjust the volume of tissue affected by an active agent. The solutions can be modified to affect any volume of tissue desired. Evidence of this is given in Example 1, with the direct injection of ethanol into feline brain. A volume of ethanol of 0.4 ml produces no toxic effects on the tissue (a circular lesion with a diameter of 2–5 mm, and a corresponding volume of 0.004–0.065 ml is found which corresponds to the location of the needle point and is typical of local mechanical disruption). The same volume of ethanol (0.4 ml) containing 5 mg (12.5 mg/ml) of carmustine produces the same result as that of ethanol alone, with no toxic effects observed. However, when a 0.05 ml volume of ethanol containing 20 mg (400 mg/ml) carmustine is injected into normal tissue, an amplification in the volume of tissue affected is observed, resulting in a large lesion with a diameter of 1–1.5 cm and volume of 1.0–1.77 ml (FIG. 1). This demonstrates that a 20–35 fold increase in the volume of tissue affected relative to the volume injected is obtained by the combination of high concentrations of carmustine to small volumes of ethanol due to the facile perfusion of the tissue with the active agent. The delivery of small/minimal volumes is an important factor in the perfusion of many tissues. For example, when injecting genes or nucleic acid derivatives directly into normal, non-neoplastic or mixed tissues large numbers of cells will become transfected due to the facile perfusion of these active agents in the tissues. The solutions developed allow the direct injection of small volumes of active agents which overcomes the dangers inherent in administering large volumes of solution into tissues, e.g. preventing leakage of the solution and as a result unwanted toxic side effects.

The present invention enables the dosing of a tissue with previously unobtainable levels of an active pharmaceutical, biological or radiotherapeutic agent and thereby produces high degrees of efficacy, i.e., greater pharmacological or biological activity than can be obtained using standard compositions and methods of delivery including systemic administration. In fact, such high levels of active agent can be perfused into tissue using the present invention that novel pharmacological effects of the active agent can be produced as demonstrated by Example 1 involving administration into normal feline brain. A combination of a small volume of ethanol (50 $\mu$l) and high concentration of carmustine (200 or 400 mg/ml) resulted in the destruction of a relatively large volume of tissue consisting of post-mitotic cells. This surprising and novel pharmacological action of carmustine was previously not attainable using known methods of administration. The well known pharmacological action of carmustine (as seen in lower concentrations of 3.3 mg/ml) is dependent upon the cells undergoing mitosis. The production of this novel pharmacological effect of high carmustine concentrations when formulated according to the current invention on post mitotic cells results in the ablation of the injected tissue as seen in the brain and also the liver and prostate (Examples 1,3,4). Such an effect can be useful in the safe ablation of pathologic regions of the brain, e.g., in Parkinsons disease or in epilepsy. It can also be employed for the safe ablation of the prostate, e.g., in prostate cancer where diffuse cancer cells are spread throughout normal prostate tissue.

It must also be appreciated that like the novel pharmacological actions of carmustine at high concentrations in the solvents described, novel actions (distinct from their known biochemical or pharmacological effects) of other active agents (such as those described below) will result, due to their delivery at concentrations never before achieved. For example, an active agent which typically must be given chronically to sustain its pharmacological action might in addition to exhibiting a completely new pharmacological action (as in the example with carmustine) achieve a sustained or irreversible effect with a single large dose.

By permitting the facile perfusion of high levels of active agents throughout tissues the compositions and intra-tissue injection methods of the present invention can be used to identify novel pharmacological and biochemical actions of an active agent; i.e., actions which heretofore were unknown or unobtainable in medical practice. Methods utilizing in vivo tissues (as described in Examples 1,3,4) as well as ex vivo tissue preparations including whole organs, organ sections, tissue slices, cell spheroids, and other tissue culture preparations can be used to identify novel effects of active agents.

The solutions of the present invention can be modified in their concentration of active agent in order to selectively affect abnormal tissue components or foreign elements following the direct injection of the solutions into the tissue regions. In Example 2, 100% ethanol and 3.3 mg/ml carmustine is shown to selectively kill tumor cells. In normal tissues, as shown in Examples 1 and 4, solutions containing carmustine up to 100 mg/ml in brain and up to 50 mg/ml in liver produce no toxic effects. Therefore, non-neoplastic and mixed tissue can be perfused with solutions having selected active agent concentrations that do not affect normal tissue, but affect abnormal tissue components or foreign elements (FIGS. 2 and 3).

Examples of selective effects include the delivery of a solution containing a hormone or angiogenic active agent, which actions are limited to cells bearing the complementary receptor. Another example is the use of an anti-infectious agent, with actions limited to infected cells and/or an extracellular infectious agent.

Pharmaceutical, biotherapeutic (biological), or radiotherapeutic active agents may be employed in practicing the present invention. Examples of pharmaceutical active agents which can be used with the present invention include, but are not limited to: anti-infective agents (cefuroxime, tetracycline), alpha adrenergic agonists (apraclonidine hydrochloride), Alzheimers disease management agents (physostigmine, tacrine hydrochloride, indomethacin), amino acids (p-aminobenzoic acid), central nervous system agents (amphetamine, haloperidol, phenytoin), amyotrophic lateral sclerosis therapeutic agents (vitamin E, riluzole), analgesics (acetaminophen, fentanyl, aspirin), anesthetics (cocaine, lidocaine, ethyl chloride), anorectal products, appetite suppressants (mazindol), antacids (cimetidine, ranitidine) anti-arthritic agents (indomethacin, ibuprofen, ketoprofen), anticonvulsants (diazepam, ethotoin, felbamate), antidepressants (fluoxetine, bupropion), antidiabetic agents (acetohexamide, glyburide), antidiuretics (vasopressin), antidotes (naloxone, physostigmine), antifibrosis therapy agents, antiglaucomatous agents (demecarium bromide), antihistamines and combinations (astemizole, chlorpheniramine), anti-inflammatory agents (indomethacin, ibuprofen, ketoprofen) antimetabolites (mercaptopurine), antineoplastics (carmustine, cisplatin, tamoxifen), anti-Parkinsonian agents (hyoscyamine, bromocriptine mesylate), antiperspirants, antipsychotic medications (haloperidol, lorazepam), antirheumatic agents, benign prostatic hyperplasia therapy (doxazosin mesylate, finasteride), nutritionals (vitamin E, vitamin D3), cardioprotective agents, cardiovascular agents (atenolol, bisopropol, digitoxin), antitoxins, cerebral metabolic enhancers, otic preparations (nystatin, chloramphenicol), cholinesterase inhibitors, contraceptives (progesterone, nifedipine), cystic fibrosis management (ibuprofen, chloramphenicol), cytoprotective agents, diagnostics (ethiodized oil, hyoscyamine sulfate), dopamine receptor agonists (bromocriptine, pergolide mesylate) emergency kits, endometriosis mangement, erectile dysfunction therapy, fertility agents (bromocriptine, clomiphene), galactorrhea inhibitors (bromocriptine), blood modifiers (dipyridamole), gastrointestinal agents (cimetidine, hyoscyamine sulfate), gout preparations (naproxen, allopurinol), homeopathic preparations, hormones (progesterone, estradiol), hypercalcemia management (hydrocortisone, paramethasone), hypocalcemia management, immunosuppresives (cyclosporin A, tacrolimus), mast cell stabilizers, migraine preparations (atenolol, ibuprofen), motion sickness products (meclizine), multiple sclerosis management (methylprednisolone, hyoscyamine sulfate), muscle relaxants (diazepam, carisoprodol), narcotic detoxification agents, nasal preparations (guaifenesin), nucleoside analogues (zidovudine, stavudine), ophthalmic preparations (suprofen, diclofenac sodium), osteoporosis preparations(estradiol), oxytotics (dinoprostone), parasympatholytics (yohimbine), parasympathomimetics, phosphate binders, porphyria agents, prostaglandins (alprostadil, dinoprostone), psychotherapeutic agents (haloperidol, droperidol), radiopaque agents (ethiodized oil), resins—ion exchange, respiratory drugs (astemizole, salmeterol xinafoate) salt substitutes, sclerosing agents (phenol), sedatives and hypnotics (haloperidol, chloral hydrate), skin and mucus membrane agents (coal tar, phenol), smoking cessation aids, sympatholytics (methysergide), Tourettes syndrome agents (haloperidol), tremor preparations (diazepam, hyoscyamine sulphate), urinary tract agents (hyoscyamine), uterine relaxants, vaginal preparations (sulfanilamide, estradiol), vasodilators (dipyridamole, papaverine hydrchloride), angiogenics, anti-angiogenics (thalidomide), apoptosis inducers (aspirin, phenethyl isothiocyanate), apoptosis inhibitors, steroids (testosterone, estradiol, triamcinolone benetonide), oxidants, anti-oxidants (vitamin E), imaging agents (iodized oil, iocetamic acid), anti-coagulants (dipyridamole, dicumarol), coagulants, anti-emetics (dimenhydrinate), anti-hypertensives (atenolol), asthma products (albuterol), diuretics (chlorothiazide), hypoglycemics, prodrugs (temozolamide), enzyme inhibitors (indinavir sulfate), anti-edema agents (chlorothiazide), radiosensitizers, vitamins (vitamin A, vitamin E), retinoids (allrans retinoic acid, cis retinoic acid) and functionally effective derivatives thereof and combinations thereof.

Useful biotherapeutic active agents include monoclonal antibodies (e.g., abciximab), monoclonal antibody cytotoxic conjugates of drugs and toxins, for example, ricin A chain or pokeweed antiviral protein; cytokines, biologic response modifiers (e.g., filgrastim), lymphokines, interferons (e.g., interferon alfa 2A), interleukins, growth factors, growth factor inhibitors, natural recombinant and synthetic proteins (e.g., adenoviral E1b 55 Kd protein, proteinase inhibitor (human) A), angiogenics (e.g., vascular endothelial growth factor, basic fibroblast growth factor), anti-angiogenics (e.g., angiostatin), vaccines (e.g., poison ivy extract), enzymes (e.g., pancreatin, dornase-alfa), peptides, genes, nucleic acids and their functional equivalents. In such cases where active agents such as peptides, proteins, enzymes, nucleic acids and the like do not inherently possess proper solubility characteristics in their natural form, agents can be made more soluble in the organic solvent vehicles of the invention by incorporating suitable amino acid residues or sequences into their molecular architecture, or by direct chemical modification. An example of this is reported in "Inhibition of acquired immunodeficiency syndrome virus by oligodeoxynucleoside methyl phosphonates", Sarin et al, (Proceedings of the National Academy of Science, USA, 85 (1988), pp 7448–7451), where antisense nucleic acid analogs with suitable organic solvent solubility characteristics were synthesized.

Useful radiotherapeutic active agents include radioisotope labeled monoclonal antibodies, other radioisotope labeled cell specific homing agents and metabolites exhibiting specific preference for specific cells or extracellular components and radioisotope labeled agents not displaying any specific cell or extracellular component homing selectivity but having the solubility characteristics of the present invention.

Distribution of the solution within the tissue and the effects of the active agent upon the tissue can be monitored with the use of an imaging method such as ultrasound, MRI (magnetic resonance imaging), or CT (computed tomography). Contrast agents can also be included for use with the appropriate imaging devices including ultrasound, CT, MRI, and PET (positron emission tomography), provided they are compatible with the solvents and active agents used in the invention. Contrast agents include such materials as iodized oil (lipiodol), iocarmic acid, iodamide, iocetamic acid, iobenzamic acid for use with CT, gadodiamide, gadopentetic acid, gadoteridol, for use with MRI, and air bubbles for ultrasound.

Many of the specific active agents in current use have been in part chosen because of their high water solubility, thereby allowing them to be administered according to standard prior art delivery techniques. In accordance with the present invention, however, highly effective active agents can be designed whose molecular architecture has been optimized for solubility, stability and/or bioavailability in one or more of the water miscible organic solvent vehicles of the invention. The present invention therefore, defines a novel approach of rational drug design, formulation and delivery.

Where the active agents to be employed can remain effectively stable, bioavailable and can be solubilized to therapeutically effective concentrations, and where the organic water miscible solvent vehicle can maintain its tissue penetrating ability in the presence of aqueous or lipoidal substances, said solvent vehicle can also tolerate the presence therein of such aqueous or lipoidal substances. Accordingly, where this circumstance is encountered, it is contemplated that the water miscible organic solvent vehicles of the present invention can also contain such aqueous or lipoidal substances up to that concentration at which significant loss of a) the solvents ability to permeate the tissue, or b) stability, bioavailability or solubility of the active agent occurs. Obviously, the maximum concentration of aqueous or lipoidal substances to be tolerated in the water miscible organic solvent vehicles of the invention can vary widely as a function of the specific aqueous and/or lipoidal substance(s) to be included, the specific active agent, the organic solvent vehicle, and the active agent concentration to be formulated. Thus, it is not possible to state a specific maximum tolerable concentration of such aqueous or lipoidal substance in the organic solvent vehicles which will be valid for all possible solutions within the scope of this invention.

Although the method described preferably uses a needle to deliver the solution, an implantable device may also be utilized. However, any such device must permit the vehicle and active agent to exit at similar rates so as to permit the organic solvent vehicle to convey therapeutically effective doses of the agent throughout the tissue. Needle delivery has the advantage of accessing a large treatment volume while requiring only a small incision.

The invention is illustrated by the following non-limiting examples.

EXAMPLE 1

Normal Feline Brain Model

Materials and Methods

Mongrel cats weighing 2.5–3.0 kg were obtained from Liberty Research, Waverly, N.Y. Animals were anaesthetized using intramuscular acepromazine at 0.1 mg/kg, followed by 0–30 mg total dose of ketamine. A small incision was made over and extending posteriorly from the coronal suture. A 3 mm burr hole was made 0.75 cm posterior to the coronal suture and 0.75 cm lateral to the midline. Using a stereotactic frame, solutions were injected at a depth of 0.75 cm in the area of the sensory cortex. The burr hole was closed with bone wax and the skin closed with a skin clip. Doses of carmustine between 5 and 20 mg were administered in dehydrated alcohol volumes of between 0.05–0.4 ml. Two weeks post injection animals were sacrificed, the brain removed in toto and fixed in 10% buffered formalin and the brain examined grossly for lesions at the site of injection. Solutions injected consisted of an ethanol solvent vehicle alone, or containing varying concentrations of carmustine.

Results

The results of Example 1 are summarized in Table 1. A volume of ethanol of 0.4 ml directly injected into the brain produced no toxic effects on the tissue (a circular lesion with a diameter of 2–5 mm, and a corresponding volume of 0.004–0.065 ml is found which corresponds to the location of the needle point and is typical of local mechanical disruption). The injection of the same volume of ethanol (0.4 ml) containing 5 mg (12.5 mg/ml) of carmustine has the same result as direct injection of ethanol alone, with no toxic effects observed. However, when 0.05 ml volumes of ethanol containing respectively 10 and 20 mg (200 and 400 mg/ml) carmustine are injected into the brain tissue, an amplification effect in the volume of tissue effected is observed, resulting in large lesions with a diameter of 1×0.8 and 1–1.5 cm respectively, and volume of 1.0–1.77 ml. This example establishes that a 20–35 times increase in the volume of tissue effected relative to the volume injected is obtained by the combination of high concentrations of carmustine to small volumes of ethanol due to facile perfusion of the tissue with the active agent. The construction of solutions which possess the same properties of facile diffusion are essential to the delivery of active agents to tissues where large volumes of solutions are impossible or dangerous to administer. In addition, a novel activity of carmustine against non-dividing cells was elicited by the 200–400 mg/ml solutions injected intratissue.

EXAMPLE 2

Walker 256 Subcutaneous Tumor Model

Materials and Methods

Tumor fragments derived from serially transplanted Walker 256 tumors were prepared and transplanted subcutaneously into female Harlan Sprague Dawley rats. Once the tumors reached appropriate size, animals were randomized into treatment groups of 5 or 6 animals and an untreated control group of 10 animals. Tumor volume for each animal was calculated using the formula: volume=(l×w2)/2. Observations included daily visual observation of each animal's general health, tumor measurements three times per week and weight every week. These measurements continued until: efficacy was apparent, the animal was terminal, the tumor became necrotic, tumor interfered with the animal's ability to eat or drink, or ten weeks beyond commencement of dosing.

Fifty rats bearing tumors ranging from 550 to 1634 mm$^3$ were randomly divided into eight treatment groups and 2 control groups. The following treatments were respectively administered to the eight treatment groups:

| Group I | 5% tumor volume absolute ethanol (10 mg/tumor carmustine) |
| Group II | 10% tumor volume absolute ethanol (10 mg/tumor carmustine) |
| Group III | 25% tumor volume absolute ethanol (10 mg/tumor carmustine) |
| Group IV | 50% tumor volume absolute ethanol (10 mg/tumor carmustine) |
| Group V | 10% tumor volume absolute ethanol (33 mg/ml carmustine) |
| Group VI | 100% tumor volume absolute ethanol (3.3 mg/ml carmustine) |

-continued

| Group VII | 100% tumor volume absolute ethanol & water (3.3 mg/ml carmustine) |
| Group VIII | 100% tumor volume water (3.3 mg/ml carmustine) |

The control animals received no treatment.

Results

Subcutaneous injection of a solution of 100% tumor volume of absolute ethanol containing 3.3 mg/ml carmustine into the tumor containing area resulted in 4/5 complete regressors, compared to 0/5 in the control group and a 29.5 day delay in tumor growth in 2 animals (one of which completely regressed before recurring), compared to a 2.8 day delay in tumor growth in the control group. The three remaining animals which received 100% tumor volume ethanol and 3.3 mg/ml carmustine were tumor free at sacrifice (Table 2). There was no evidence of scar, hair loss or residual redness in the area of the tumor demonstrating the selective toxicity of this solution for tumor tissue.

EXAMPLE 3

Normal Canine Prostate Model

Materials and Methods

Random-source adult male canines were used in this experiment. All animals had a palpable prostate gland consistent with an adult-sized canine gland. The animals had free access to water and were fed on a standard schedule.

Body surface area (m2) was calculated for each animal using published tables.

On the day of surgery, the animals were preanesthetized with acepromazine (0.22 mg/kg) and atropine (0.05 mg/kg) intramuscularly. General anesthesia was induced with intravenous thiopental sodium (20–25 mg/kg) and, following orotracheal intubation, was maintained with a 0.5–2.0% halothane-oxygen mixture given through a semi-closed circle system. Perioperative antibiotics consisted of intravenous gentamicin (3 mg/kg) on the day of surgery and daily intramuscular gentamicin (3 mg/kg) for seven days following surgery.

In each animal, an 8 French urinary catheter was passed per urethra into the bladder, and the bladder was filled with normal saline. A diagnostic Aloka Echo SSD650 ultrasound machine with a UST 664 5/7.5 MHZ biplanar linear array transrectal probe (Wallingford, Conn.) was used to determine the maximal axial (transverse) width, height, and midline sagittal (longitudinal) length. The length was measured in the midline from the distal most aspect of the apex to the cephalad most portion of the gland. The volume was then determined using the following formula: length× width×½ height. A lower abdominal midline incision was created, and the peritoneal cavity was entered. The bladder and prostate were exposed and the periprostatic fat was carefully dissected off of the base of the gland. Using TRUS imaging of the prostate as well as direct visualization through the peritoneotomy a three inch 20 gauge spinal needle connected to a standard 10-cc luer-lock syringe containing the appropriate aliquot for injection was guided into the base of the right lobe of the prostate. The needle tip was localized within the prostatic parenchyma with ultrasound guidance and appropriately positioned.

Animals were randomly divided into subgroups. Animals A1 and A2 received a volume of dehydrated ethanol equal to 100% of the measured prostate volume while the remaining animals received a volume of 98% dehydrated ethanol equal to 50% of the total gland volume as determined by TRUS imaging. The animals received escalating doses of Carmustine dissolved in dehydrated ethanol: A1 and A2 2 mg/ml; B1 and B2, 5 mg/ml; C1 and C2 12.5 mg/ml; D1 and D2 18 mg/ml; and E1 and E2, 25 mg/ml. All animal subgroups were injected on separate days under general anesthesia through a midline peritoneotomy approach using TRUS guidance for needle placement. The needle was initially positioned at the ventral aspect of the apex of the gland and then withdrawn from apex to base during the injection. The needle was then repositioned toward the dorsal aspect of the gland at the apex and withdrawn toward the base during the injection so that as much of the parenchyma could be covered as possible.

Fourteen days following injection all animals underwent repeat TRUS imaging of the prostate gland under general anesthesia and were then euthanized by exsanguination under deep general anesthesia. The bladders and prostates were excised enbloc and fixed in formalin. If there was any evidence of perirectal inflammation or suspicion of pathology a section of the rectum was removed for pathologic examination. After adequate tissue fixation in formalin, the prostate glands were step sectioned and the volume of the prostate parenchyma affected (cm3) was calculated and quantitated based on the measured length, height and thickness of individual step sections of the gland. The volumes were then added together resulting in a quantification of the total parenchymal volume affected on a prostate gland for prostate gland basis. The tissue was then submitted for histopathologic interpretation.

Results

All animals had heterogeneous TRUS patterns with echolucent areas within the prostatic parenchyma 14 days after injection that correlated with areas of hemorrhagic and coagulative necrosis identified on step sections of the glands. The urethra in all of the animals showed evidence of submucosal hemorrhage, mucosal erosion and inflammation. There was no evidence of extraprostatic extravasation during the injections, there were no rectal injuries, or episodes of urinary incontinence, and no animal required analgesics beyond 48 hours after injection.

Figure 4:
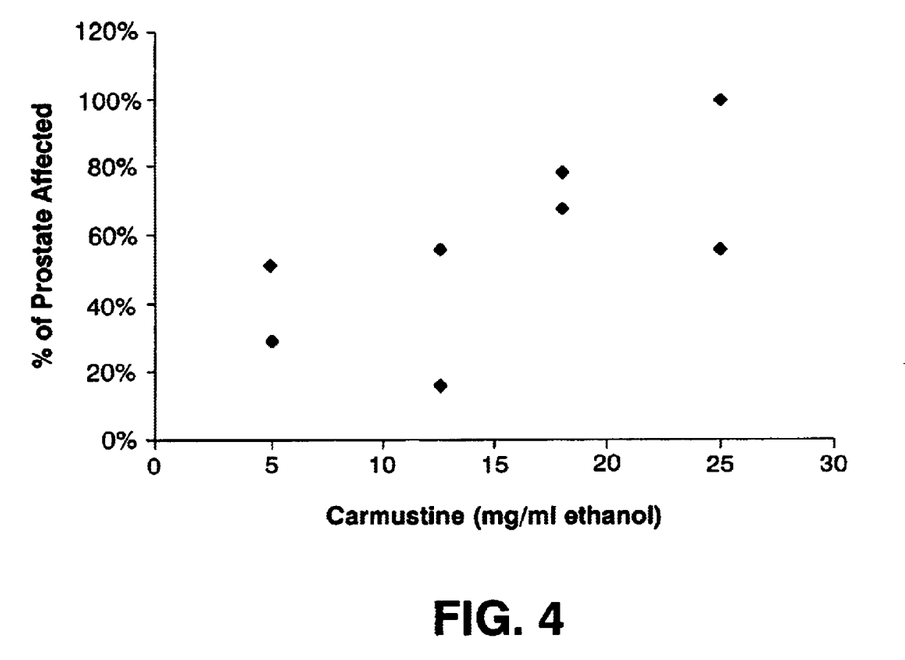
FIG. 4 is a graph depicting correlation of carmustine concentration (mg/ml in ethanol) injected in a volume of 50% prostate volume with the percent of prostatic tissue affected at two weeks post-injection.

The volumes of tissue affected by equal concentrations of carmustine varied widely. However, the highest concentrations of carmustine were associated with the largest volumes of tissue affected (Table 3 and FIG. 4).

EXAMPLE 4

Normal Rat Liver Model

Materials and Methods.

54 male Sprague-Dawley rats 250–300 g in body weight were caged in groups of 2 by treatment group, in standard animal housing facilities and given free access to food and water. Prior to surgery, animals received 0.2 ml intramuscular injection of ketamine and xylazine (30 mg/kg and 4 mg/kg respectively). Rats were anesthetized and fixed on a restraining board. The right upper quadrant of the abdomen was shaved and prepped with betadine solution. A lateral incision approximately 1 cm in length was made 2 cm to the right of the abdominal mid-line and 2 cm below the last rib on the right side and the liver exposed. Under direct visual observation, the solution was injected into the liver slowly over a period of about 2 minutes, using a Hamilton microliter syringe (702) equipped with a 27 gauge needle. The needle was withdrawn and the abdominal incision closed using 4-0 plain gut to seal the peritoneum and skin clips to close the skin. Observations of each animal were made hourly for 4 hours during the day of surgery and daily thereafter for two weeks. At two weeks the animals were sacrificed and their livers examined grossly for lesions at the site of injection.

Results

The results of experiment 4 are summarized in Table 4. At an ethanol volume of 100 µl, rats appeared normal at sacrifice, with no or small lesions present upon gross examination of the liver. At an ethanol volume of 100 µl and 12.5–50 mg/ml carmustine, the rats appeared normal at sacrifice and, as with ethanol only, had no or small lesions present upon gross examination of the liver. At ethanol volumes of 100 µl and 100 mg/ml carmustine, large areas of tissue destruction were found.

TABLE 1

Normal Feline Brain Model

| Treat-Treatment | Volume (ml) | Carmustine (mg/ml) | No. of Cats | Survival (days) | Clinical Signs - Gross Findings |
|---|---|---|---|---|---|
| Ethanol | 0.2 | 0 | 2 | Term | 2 NPND both had small discolored area but no cavity |
| Ethanol | 0.4 | 0 | 3 | Term | 3 NPND -all with circular lesions, 2–3 mm, 4–5 mm, and 5 mm |
| Ethanol + 5 mg Carmustine | 0.05 | 100 | 1 | Term | NPND 2–3 mm area of discoloration with small central cavity |
| Ethanol + 10 mg Carmustine | 0.05 | 200 | 1 | Term | Circles to left, otherwise normal - large lesion 1 × 0.8 cm |
| Ethanol + 20 mg Carmustine | 0.05 | 400 | 1 | 3 days | Died - large 1–1.5 cm circular discolored soft necrotic area |
| Ethanol + 10 mg Carmustine | 0.1 | 100 | 1 | Term | NPND - 4–5 mm circular lesion |
| Ethanol + 5 mg Carmustine | 0.2 | 25 | 1 | Term | NPND - 4 mm circular lesion |
| Ethanol + 5 mg Carmustine | 0.4 | 12.5 | 1 | Term | NPND - 2–3 mm circular lesion |

NPND = No perceptible neurological deficit

TABLE 2

Walker 256 Subcutaneous Model in Rats

| Group | Treatment | Mean Days to Tumor Size 5000 mm³ after treatment | Complete Regressors/ Total | Tumor Free at Time of Death |
|---|---|---|---|---|
| I | Untreated control | 2.8 | 0/5 | 0 |
| VI | Carmustine 3.3 mg/ml Alcohol 100% tumor volume | 29.5 (day 71) | 4/5 | 3 |

TABLE 3

Prostate gland volume, dose of carmustine injected (mg/ml ethanol), volume of prostate affected and involvement of periprostatic tissues for animals who received dehydrated ethanol at 50% of prostate volume and escalating doses of carmustine.

| Prostate Volume by TRUS (cc³) | Carmustine Concentration (mg/ml Ethanol) | Volume Affected Left/Right/ PU (cc³) | Periprostatic Tissue Involvement |
|---|---|---|---|
| 9.8 | 5 | 1.61/0.85/2.51 | Cystic necrosis R periurethral |
| 8.42 | 5 | 0.68/1.73/0 | Marked fat necrosis |
| 20.16 | 12.5 | 1.8/1.4/0 | Minimal fat necrosis |
| 4.36 | 12.5 | 1.8*/0.62 | Moderate fat necrosis |
| 27.75 | 18 | 8.35/12.31/1.2 | Marked fat necrosis |
| 37.2 | 18 | 11.76/9.73/3.84 | Marked fat necrosis |
| 22.14 | 25 | 7.5/4.8/0 | Mild fat necrosis |
| 32.64 | 25 | 32.64** | Large pelvic abscess |

PU = periurethral
*left + right
**left + right + periurethral

TABLE 4

Normal Rat Liver Model.

| Treatment | Volume (µl) | Carmustine (mg/ml) | No. of Rats | Survival | Clinical Signs (Gross Findings) |
|---|---|---|---|---|---|
| Ethanol | 100 | — | 6 | term | 6 ANAS, All with small lesion |
| Ethanol + 1.25 mg carmustine | 100 | 12.5 | 2 | term | ANAS, no lesion |
| Ethanol + 2.5 mg carmustine | 100 | 25 | 2 | term | ANAS, both with very small lesions |
| Ethanol + 5 mg carmustine | 100 | 50 | 2 | term | ANAS, both with small lesions |
| Ethanol + 10 mg 10 mg carmustine | 100 | 100 | 2 | term | Less active & responsive at sacrifice. Large areas tissue destruction. |

ANAS (appeared normal at sacrifice).

What is claimed is:

1. A method for delivering an antineoplastic agent to a normal or non-neoplastic solid tissue which comprises:
   injecting directly into said solid tissue a therapeutically effective volume of a solution comprising a pharmaceutically acceptable water miscible organic solvent and a therapeutically effective amount of said antineoplastic agent;
   said solution having a partition coefficient of at least about 0.1; and
   said antineoplastic agent being stable and bioavailable in said solution;
   wherein the normal or non-neoplastic solid tissue is effectively perfused by the antineoplastic agent.

2. The method of claim 1 which comprises injecting an amount of said solution sufficient to treat a pre-selected abnormal tissue component in said non-neoplastic tissue.

3. The method of claim 1 which comprises injecting an amount of said solution sufficient to treat a pre-selected foreign element in said non-neoplastic tissue.

4. The method of claim 1 which comprises injecting an amount of said solution sufficient to treat in said non-neoplastic tissue at least two treatment targets selected from a pre-selected normal tissue component, a preselected abnormal tissue component and a preselected foreign element.

5. The method of claim 1 which comprises injecting a volume of said solution smaller than a volume of the tissue treated.

6. The method of claim 1 wherein said antineoplastic agent comprises BCNU.

7. The method of claim 1 wherein said solvent comprises ethanol.

8. The method of claim 7 wherein said ethanol comprises absolute ethanol.

9. The method of claim 1 wherein the antineoplastic agent comprises a pharmaceutical agent.

10. The method of claim 1 wherein the antineoplastic agent comprises a biological agent.

11. The method of claim 1 wherein the antineoplastic agent comprises an angiogenic agent.

12. A method for delivering an antineoplastic agent to a non-neoplastic solid tissue which comprises:

injecting into an area adjacent to said solid non-neoplastic tissue a therapeutically effective volume of a solution comprising a pharmaceutically acceptable water miscible organic solvent and a therapeutically effective amount of said antineoplastic agent;

said solution having a partition coefficient of at least about 0.1; and said antineoplastic agent being stable and bioavailable in said solution;

wherein the non-neoplastic solid tissue is effectively perfused by the antineoplastic agent.

13. The method of claim 12 wherein said area is one of a normal tissue area, a neoplastic tissue area and a cavity.

14. The method of claim 13 wherein said cavity is one of a naturally occurring boy cavity and a cavity formed by surgical resection.

15. The method of claim 12 which comprises injecting an amount of said solution sufficient to treat a pre-selected abnormal tissue component in said non-neoplastic tissue.

16. The method of claim 12 which comprises injecting an amount of said solution sufficient to treat a pre-selected foreign element in said non-neoplastic tissue.

17. The method of claim 12 which comprises injecting an amount of said solution sufficient to treat in said non-neoplastic tissue at least two treatment targets selected from a pre-selected normal tissue component, a preselected abnormal tissue component and a preselected foreign element.

18. The method of claim 12 which comprises injecting a volume of said solution smaller than a volume of the tissue treated.

19. The method of claim 12 wherein said antineoplastic agent comprises BCNU.

20. The method of claim 12 wherein said solvent comprises ethanol.

21. The method of claim 20 wherein said ethanol comprises absolute ethanol.

22. The method of claim 12 wherein the antineoplastic agent comprises a pharmaceutical agent.

23. The method of claim 12 wherein the antineoplastic agent comprises a biological agent.

24. The method of claim 12 wherein the antineoplastic agent comprises an angiogenic agent.

25. A method for delivering an antineoplastic agent to a normal or non-neoplastic solid tissue which comprises:

preparing a therapeutically effective volume of a solution consisting essentially of a pharmaceutically acceptable water miscible organic solvent and a therapeutically effective amount of said antineoplastic agent, said solution having a partition coefficient of at least about 0.1, and said antineoplastic agent being stable and bioavailable in said solution; and injecting said volume of said solution directly into said solid tissue;

wherein the normal or non-neoplastic solid tissue is effectively perfused by the antineoplastic agent.

* * * * *